United States Patent [19]

Widder

[11] Patent Number: 5,214,963
[45] Date of Patent: Jun. 1, 1993

[54] METHOD AND APPARATUS FOR TESTING INNER LEAD BONDS

[75] Inventor: David C. Widder, Billerica, Mass.

[73] Assignee: Digital Equipment Corporation, Maynard, Mass.

[21] Appl. No.: 722,845

[22] Filed: Jun. 28, 1991

[51] Int. Cl.⁵ .............................. G01N 3/08
[52] U.S. Cl. .............................. 73/827
[58] Field of Search ............ 73/827, 37, 840, 842

[56] References Cited

U.S. PATENT DOCUMENTS 3,559,054  1/1971  Bowers ..................... 73/37 X
3,581,557  6/1971  Drees et al. ............. 73/827 X
4,771,666  9/1988  Ikeuchi et al. .......... 83/98 X

*Primary Examiner*—Jerry W. Myracle
*Attorney, Agent, or Firm*—Arnold, White & Durkee

[57] ABSTRACT

A process for nondestructive testing of beam lead bonds in disclosed. A high pressure liquid jet is applied to the beam leads adjacent the bond pad such that a force is applied to the lead in the opposite direction of the bonding step. If the bond does not have sufficient strength, the lead is bent away from the bonding pad and can be detected either visually or electrically. If the bond does have sufficient strength to withstand the force, no degradation of the bond occurs.

20 Claims, 1 Drawing Sheet

METHOD AND APPARATUS FOR TESTING INNER LEAD BONDS

BACKGROUND OF THE INVENTION

1. Field of the Invention

The present invention relates to processes and apparatus for testing the sufficiency of lead bonds. More particularly, the invention relates to nondestructive test methods for TAB tape bonds to semiconductor chips.

2. Prior Art

Long term reliability of packaged semiconductor devices is dependent, among other things, on the integrity of the inner lead bond. Strength testing of lead bonds is based on the assumption that if the bond can withstand a minimum prescribed load, it is a joint that will not fail in normal use throughout the life of the product.

The inner lead bonding process on semiconductor devices has, in the past, been accomplished with wire bonding. This process has an inherent built in quality assurance opportunity in that as each wire is bonded, the bonding machine can give a slight controlled pull on the bonded wire thus assuring that the joint can at least withstand this predetermined force.

As device lead counts have increased and bonding densities have been increased, the industry has been moving towards tape automated bonding ("TAB") technology where the interconnecting wire is replaced with a prefabricated tape with the appropriate lead pattern formed on the tape. The leads have a generally rectangular cross-section and are bonded to the die by thermal compression.

The TAB process does not offer the built in bond process assurance of wire bonding since there is no way for the bonding machine to pull on the individual leads after the bonding step. Current test methods for TAB leads involve the manual utilization of a hook to pull representative samples of the bonded leads. This process is very slow and only permits random sampling to be conducted. Further, hook testing results destruction of the leads being tested.

It would be a significant advancement in the art to provide an apparatus and method for automatically testing TAB bonds. It would be an even further advancement if such apparatus and method provided for essentially 100% bond integrity verification and was nondestructive. The present invention provides an apparatus and method which achieve these advantages and others which will become more fully apparent from the following description and appended claims.

SUMMARY OF THE INVENTION

The present invention uses a high pressure jet of liquid, such as water, to impinge on the TAB lead at the edge of the silicon die body. The force of the liquid jet is directed in the opposite direction from the bonding process such that it tends to apply a lifting force to the bonded lead.

The liquid jet is sized such that its diameter at the point of impingement is no greater than the width of the narrowest TAB lead that will be encountered. The sizing of the jet assures that the impingement force is independent of the width of the lead.

The liquid jet is preferably applied immediately after the bonding step in a continuous or incremental motion around the edge of the die. If a bond site has less than the minimum required retention strength, the bond will open and the lead will lift such that the failure is easily detectable, either visually or electrically. If the bond has sufficient strength to withstand the impingement force, no degradation to the bonded joint will occur. Detached leads can usually be rebonded to their pads.

BRIEF DESCRIPTION OF THE DRAWINGS

The invention is best understood by reference to the following detailed description of the preferred embodiments when read in conjunction with the accompanying drawings in which like elements have been given like numerals, and wherein.

DETAILED DESCRIPTION OF THE PREFERRED EMBODIMENTS

Figure 1:
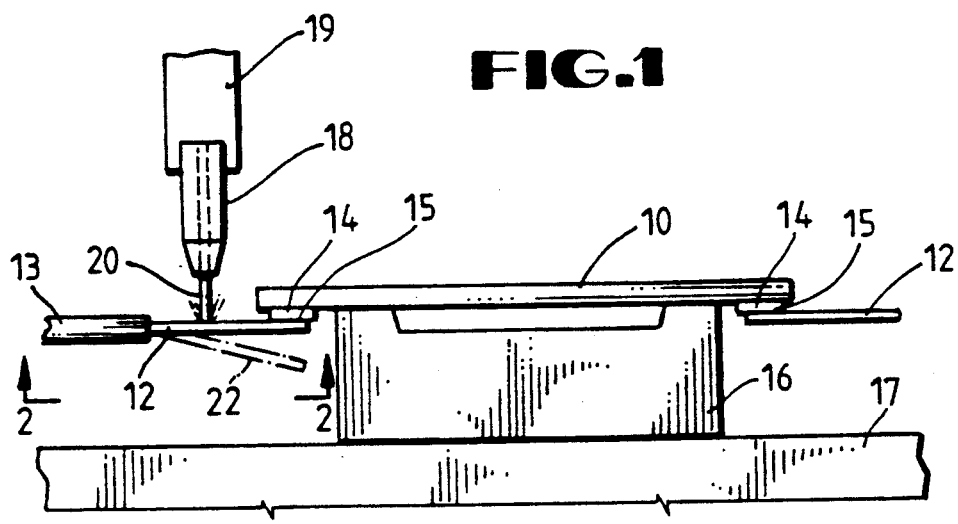
FIG. 1 is a schematic side view of a bonded lead being tested according to the present invention.
Figure 2:
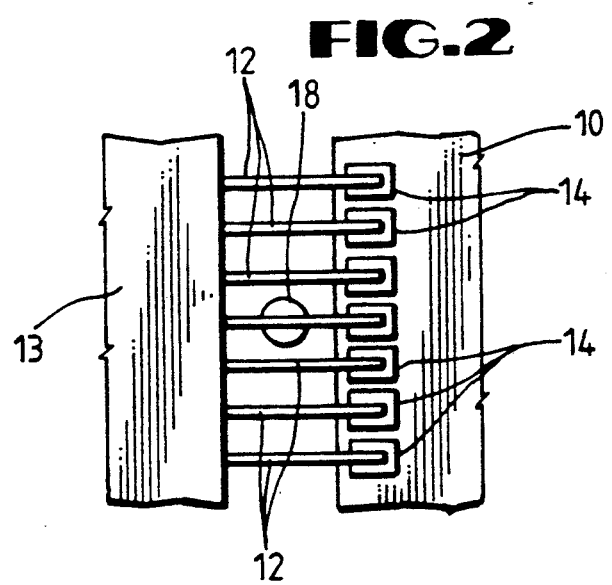
FIG. 2 is a schematic view of a portion of a semiconductor device illustrating use of the present invention to test leads bonded to the device.

The present invention provides a nondestructive method for testing the integrity of thermal compression bonded joints such as TAB bonds to ensure that they are adequate to provide long term device reliability. The invention is best understood by reference to FIGS. 1 and 2 which illustrate a silicon chip 10 having a plurality of leads 12 bonded to pads 14 to form bonded joint 15.

In the preferred embodiment, leads 12 are beam leads from a tape automated bonding ("TAB") tape 13 which have been attached to pads 14 on chip 10 by thermal compression bonding.

Chip or die 10 is placed in a suitable test platform such that it is supported by a chuck 16 or other suitable device carrier. Chuck 16 is supported by an x-y positioning table 17. A nozzle 18 attached to hose 19 is positioned in the test apparatus such that it can apply a high pressure liquid jet 20 to leads 12. Preferably, liquid jet 20 is applied to leads 12 near the edge of chip 10 adjacent joint 15 to force lead 12 away from chip 10. In the preferred embodiment, liquid jet 20 is applied in the opposite direction from the bonding process. Positioning table 17 allows chip 10 to be moved automatically so that liquid jet 20 impinges each lead 12.

If the bond joint 15 has less than the minimum required retention strength, the bond will open and lead 12 will lift as illustrated by lead 22 such that the failure is easily detectable by visual examination. Visual inspection can be accomplished with or without magnification. Additionally, various automated systems for detecting separated bonds can be utilized as can electrical tests of the circuitry. Detached leads can then be reconnected to their respective pads.

It has been found that for TAB leads having a width of about 0.002 inches, a bond loading force threshold seems to exist at about 8 grams. That is, if the bond does not fail with the application of an 8 gram load, it will not fail during normal stress testing. Accordingly, in the preferred embodiment of the present invention, liquid jet 20 applies about an 8 gram force to lead 12. However, it will readily be appreciated that other forces can and should be used according to the actual device characteristics. For example, with narrower leads or a soft lead material, the force would have to be reduced to prevent the liquid jet from cutting or otherwise damaging the lead.

The diameter of liquid jet 20 should be smaller than the minimum beam width so that the force applied to the leads is not affected by beam width variations. For beam leads having widths in the range of 0.002 plus or minus 0.0005 inches, the preferred liquid jet diameter is about 0.0015 inches.

In the preferred embodiment, deionized water is used for liquid jet 20. It is inexpensive, readily available and does not contaminate the die or leads. Of course, other suitable liquids can also be used.

Liquid jet 20 is preferably applied immediately after the bonding step during package assembly. Chip 10, in its carrier, is placed in the test chamber and liquid jet 20 is applied to leads 12 as chip 10 is moved in a continuous motion by positioning table 17. Alternatively, while the preferred embodiment is to move chip 10, it will be appreciated that a suitable apparatus can also be built in which chip 10 is maintained stationary and nozzle 18 is moved such that liquid jet 20 impinges each of the leads 12. Further, movement of chip 10 or nozzle 18 can be done incrementally rather than in a continuous motion.

While the invention has been described with respect to the presently preferred embodiments, it will be appreciated by those skilled in the art that many modifications or changes can be made without departing from the scope or essential characteristics of the invention. For example, while the invention is especially suited for TAB leads, it can also be applied to other systems. Accordingly, the foregoing description is meant to be illustrative and not restrictive and the following claims are intended to embrace all such modifications and changes.

What is claimed is:

1. A process for verifying the integrity of lead bonds comprising the steps of:
   placing a device having leads bonded thereto in a test apparatus;
   impinging said leads with a liquid jet at a point adjacent said bonds and in a direction such that a predetermined force tending to separate said bonds is applied to said leads, said liquid jet having a diameter at the point of impingement which is less than or equal to the width of the narrowest of said leads; and
   determining whether any of said bonds is broken.

2. A process according to claim 1 wherein said liquid is water.

3. A process according to claim 1 wherein said device has TAB leads bonded thereto.

4. A process according to claim 3 wherein said liquid jet applies a force of about 8 grams to said leads.

5. A process according to claim 1 wherein said determining step comprises visually examining said leads and bonds.

6. A process according to claim 1 wherein said determining step comprises electrically testing said device.

7. A process according to claim 1 further comprising rebonding any leads which separated from said device.

8. A process according to claim 1 wherein the direction of impingement is perpendicular to a surface to which said leads are bonded.

9. A process for verifying the integrity of inner lead bonds comprising the steps of:
   placing a device having leads bonded thereto in a test apparatus;
   applying a high pressure jet of water against said leads in a direction perpendicular to a surface to which said leads are bonded with a predetermined force such that defective bonds are separated; and
   identifying any separated bonds so that said leads can be rebonded to said device.

10. A process according to claim 9 wherein said water jet has a diameter at the point of impingement which is less than or equal to the width of the narrowest of said leads.

11. A process according to claim 9 wherein said identifying step comprises visually inspecting said leads and bonds.

12. A process according to claim 9 wherein said identifying step comprises electrically testing said device.

13. An apparatus for testing the integrity of inner lead bonds comprising:
   a support for holding a die having leads bonded thereto; and
   means for applying a liquid jet against said leads with a predetermined force at a point adjacent said bonds and in a direction perpendicular to a surface to which said leads are bonded such that it tends to separate said bonds.

14. An apparatus according to claim 13 wherein said applying means comprises a nozzle connected to a suitable liquid source.

15. An apparatus according to claim 14 wherein said nozzle produces a liquid jet having a diameter at the point of impingement which is less than or equal to the width of the narrowest of said leads.

16. An apparatus according to claim 13 further comprising means for moving said support and said applying means relative to each other such that all leads bonded to said die are tested.

17. An apparatus according to claim 16 wherein said moving means comprises an x-y positioning table.

18. An apparatus for testing the integrity of inner lead bonds comprising:
   a support for holding a die having leads bonded thereto; and
   means for applying a liquid jet against said leads with a predetermined force at a point adjacent said bonds and in a direction tending to separate said bonds, said liquid jet having a diameter at the point of impingement which is less than or equal to the width of the narrowest of said leads.

19. An apparatus according to claim 18, wherein said applying means comprises a nozzle connected to a suitable liquid source.

20. An apparatus according to claim 18, wherein said liquid jet is applied in a direction perpendicular to a surface to which said leads are bonded.

* * * * *